US008715241B2

(12) United States Patent
Edoga et al.

(10) Patent No.: US 8,715,241 B2
(45) Date of Patent: May 6, 2014

(54) NEEDLE ASSEMBLY (71) Applicant: Circuport, Inc., Morristown, NJ (US)

(72) Inventors: John K. Edoga, North Beach, NJ (US); Thierry Richard, Villiers le Mahieu (FR); Todd Ing, Wilmette, IL (US); Michael Resnikoff, Morristown, NJ (US); John Studer, Gladstone, NJ (US)

(73) Assignee: Circuport, Inc., Morristown, NJ (US)

( * ) Notice: Subject to any disclaimer, the term of this patent is extended or adjusted under 35 U.S.C. 154(b) by 0 days.

(21) Appl. No.: 13/666,621

(22) Filed: Nov. 1, 2012

(65) Prior Publication Data

US 2013/0060192 A1 Mar. 7, 2013

Related U.S. Application Data (63) Continuation of application No. PCT/US2011/034934, filed on May 3, 2011.

(60) Provisional application No. 61/439,599, filed on Feb. 4, 2011, provisional application No. 61/378,195, filed on Aug. 30, 2010, provisional application No. 61/330,775, filed on May 3, 2010, provisional application No. 61/406,839, filed on Oct. 26, 2010, provisional application No. 61/412,974, filed on Nov. 12, 2010, provisional application No. 61/383,171, filed on Sep. 15, 2010.

(51) Int. Cl.
*A61M 5/178* (2006.01)
*A61M 37/00* (2006.01)

(52) U.S. Cl.
USPC .............. 604/164.01; 604/6.16; 604/288.02; 604/93.01

(58) Field of Classification Search
USPC ................. 604/6.16, 43, 116, 117, 118, 158, 604/164.01, 164.07, 164.08, 264, 523, 533, 604/288.02
See application file for complete search history.

(56) References Cited

U.S. PATENT DOCUMENTS

| 2002/0095138 | A1 | 7/2002 | Lynch et al. | |
|---|---|---|---|---|
| 2006/0253076 | A1 | 11/2006 | Butts et al. | |
| 2007/0112303 | A1 * | 5/2007 | Liniger | 604/164.01 |
| 2007/0191771 | A1 * | 8/2007 | Moyer | 604/158 |

OTHER PUBLICATIONS

International Search Report for related international application No. PCT/US2011/034934, mailed on Aug. 2, 2011.

* cited by examiner

*Primary Examiner* — Nicholas Lucchesi
*Assistant Examiner* — Leah Stohr
(74) *Attorney, Agent, or Firm* — Day Pitney LLP

(57) ABSTRACT

Needle assemblies are disclosed. In some embodiments, the needle assembly includes a main housing including an obturator insertion opening and an opposite needle connection opening, a connector housing configured to engage the main housing, the connector housing including obturator, tubing, and plug openings, a self-sealing plug including a channel, the plug positioned within the connector housing so the channel is aligned with the tubing opening, a needle holder base, and a needle. The connector housing is configured to engage the main housing in first and second positions. The obturator opening is axially aligned with the obturator insertion opening and axially aligned with the needle in the first position. The tubing opening is axially aligned with the obturator insertion opening and in fluid connection with the needle in the second position.

20 Claims, 6 Drawing Sheets

NEEDLE ASSEMBLY

CROSS REFERENCE TO RELATED APPLICATIONS

This patent application is a continuation of and claims the benefit of priority to International Patent Application No. PCT/US2011/034934 filed May 3, 2011, which in turn claims the benefit of priority to U.S. Provisional Application Nos. 61/330,775, filed May 3, 2010, 61/378,195, filed Aug. 30, 2010, 61/383,171, filed Sep. 15, 2010, 61/406,839, filed Oct. 26, 2010, 61/412,974, filed Nov. 12, 2010, and 61/439,599, filed Feb. 4, 2011, each of which is incorporated by reference herein in its entirety for any purpose whatsoever.

BACKGROUND

Unfortunately, a significant number of individuals suffer from decreased kidney function. If the kidney function is depreciated enough, usually to approximately 10% of normal levels, an individual must either undergo kidney dialysis procedures or receive a kidney transplant. Dialysis procedures remove toxic substances, waste, and bodily fluids from the bloodstream when the kidneys are unable to do so. Presently, two types of dialysis are commonly utilized, peritoneal dialysis and hemodialysis.

Peritoneal dialysis generally involves injecting special solutions into the abdomen of a patient through a port, or plastic tube. The special solution enters the abdomen and occupies the space around the abdominal organs known as the peritoneal cavity. Wastes, toxins, and excess bodily fluids mix with the special solution and are retained therein through osmosis. Once the special solution absorbs a sufficient amount of the wastes, toxins, and excess fluids, the combination may be drained out through the port. This process can either occur every four to six hours in a manual procedure, or continuously if used in conjunction with a cycler machine. While this procedure may usually be performed at home by the patient, it will be appreciated that such a process creates a great burden on the patient, and typically interferes with normal life functioning.

Hemodialysis is conducted by circulating blood through an external filtering machine. Typically, a patient will require hemodialysis three-times per week, with each session lasting approximately four hours.

In hemodialysis, an "arterial" catheter removes blood from the body. The blood is then pumped across a semi-permeable membrane containing solutions to remove toxins, wastes, and excess bodily fluids. The cleansed blood is then returned to the body through a "venous" catheter. Other than in emergency situations, dialysis access is generally obtained through an AV fistula or AV graft. The same graft serves to both supply blood to the hemodialysis machine as well as return blood to the body. In this regard, two catheters are typically placed into the AV fistula or AV graft. The catheter closest to the heart typically serves as the "arterial" catheter, flowing blood from the body, and the downstream catheter typically serves as the "venous" catheter, returning blood to the body. Because the pressure gradient between the two needles is typically not great, the hemodialysis machine must include a pump to circulate the blood.

Because, peripheral veins are typically too small in diameter to permit the required flow of 250 milliliters of blood per minute back into the body, AV fistulas are surgically created approximately six weeks before hemodialysis begins in order to artificially enlarge a vein. This is done by joining a vein to an artery in a localized area while the patient is under anesthesia. The increased blood from the artery causes the vein to enlarge and thicken, thus permitting larger flows through the vein then would otherwise be possible. After the six weeks that the fistula needs to heal, two dialysis needles may be placed within the enlarged and thickened vein. One needle permits blood to be removed for dialysis and the other permits cleansed blood to return to the enlarged and thickened vein.

For individuals whose veins are not suitable for an AV fistula, an AV graft may be used. This procedure involves surgically grafting a portion of the patient's saphenous vein, a donor animal artery, or a synthetic conduit and using it to connect an artery to an existing vein. The grafted vein or prosthetic conduit may be double punctured to draw blood into the dialysis machine and return cleansed blood into the body.

Neither AV fistulas nor AV grafts are ideal. The resulting increased blood through the veins may cause a neo-intimal hyperplasia, which could occlude the veins and lead to access loss. Additionally, the direct flow of blood from an artery into the veins puts undue strain on the local vascular system in general, and the heart in particular. Finally, because blood is both withdrawn from and returned to the body in the same AV fistula, dialysis is typically inefficient because of the phenomenon of recirculation.

Recent dialysis advances involve the implanting of dialysis access ports beneath the skin. These ports generally contain a chamber plugged with a self-sealing material, such as rubberized silicone, with a synthetic catheter extending out from within the chamber. The port is placed under the skin and the catheter is surgically implanted into a vein. A second port can similarly implanted beneath the skin and its catheter is surgically implanted into another portion of the vein. In the case of one of these ports, the vein cannulated with both catheters was the Superior Vena Cava. One port may then be used to remove blood for dialysis while the other port is used to return the cleansed blood back to the body.

Unfortunately, even with the use of AV fistulas, AV grafts, and implanted access ports, positioning of the end of the access needle into the artery of the patient can be problematic. As a result, punctures to the artery walls and to portions of the fistulas, grafts, and access ports can occur and result in damage to the structure, which can require additional procedures to replace the damaged structure. Up to 50% of AV fistulas never mature sufficiently to be safely punctured and used as the primary access for hemodialysis. AV grafts readily develop stenoses and clots and require expensive treatments to restore patency and ports because of the designed method of use cause skin tracts to form, which lead to life threatening infections.

SUMMARY

The disclosed subject matter generally relates to a needle assembly used for extracorporeal circulation such as hemodialysis. More particularly, the disclosed subject matter relates to hemodialysis access needles for use with an implanted access port to facilitate positioning of a needle end in an artery or vein of a patient and the fluid connection of the needle to a conduit such as blood tubing.

Needle assemblies are disclosed. In some embodiments, the needle assemblies include the following: a main housing including an obturator insertion opening and an opposite needle connection opening; a connector housing configured to engage the main housing, the connector housing including an obturator opening, a tubing opening, and a plug opening; a substantially self-sealing plug including a channel formed therethrough, the plug positioned within the connector housing so the channel is aligned with the tubing opening; and a needle sub-assembly having a needle holder base and a needle, the needle holder base including first and second surfaces, the first surface configured to removably join with the needle connection opening and the second surface having the needle extending therefrom. The connector housing is configured to engage the main housing in first and second positions. The obturator opening is substantially axially aligned with the obturator insertion opening and substantially axially aligned with the needle in the first position. The tubing opening is substantially axially aligned with the obturator insertion opening and in fluid connection with the needle in the second position.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 1A:
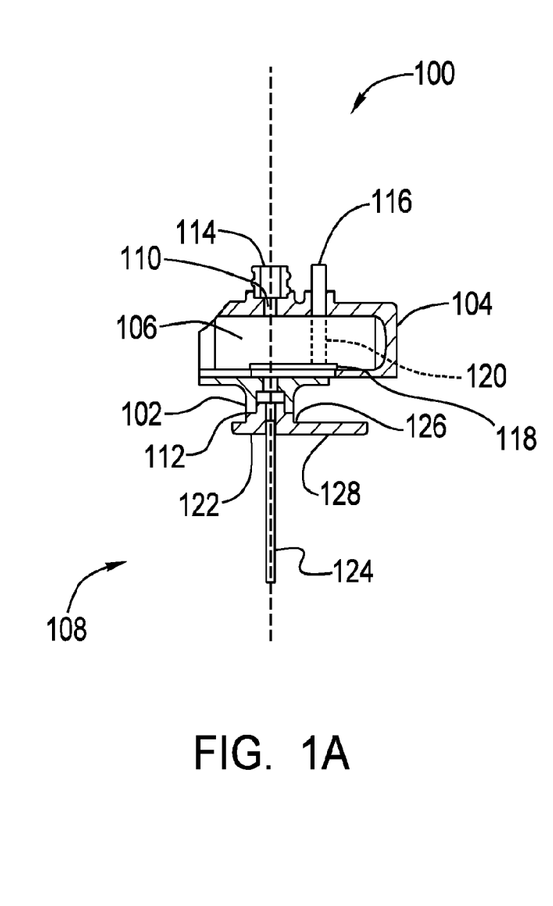
FIGS. 1A-1D are side section views of assemblies according to some embodiments of the disclosed subject matter.
Figure 1B:
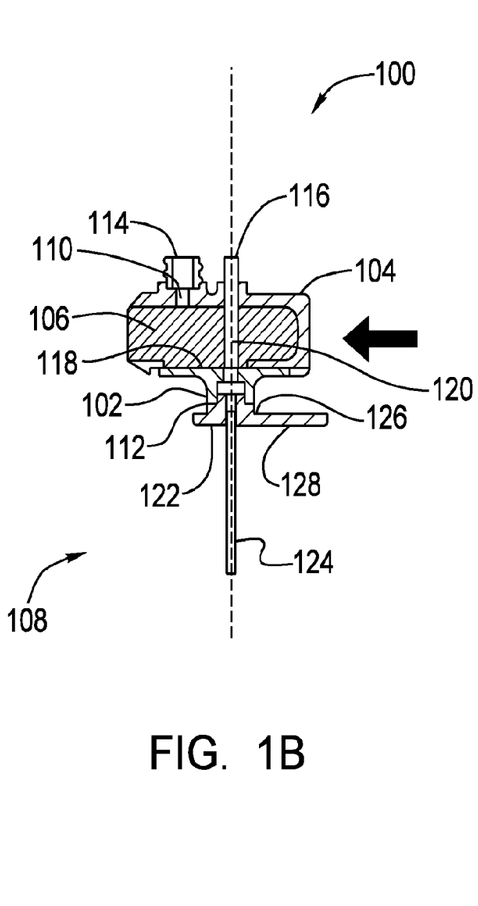
Figure 1C:
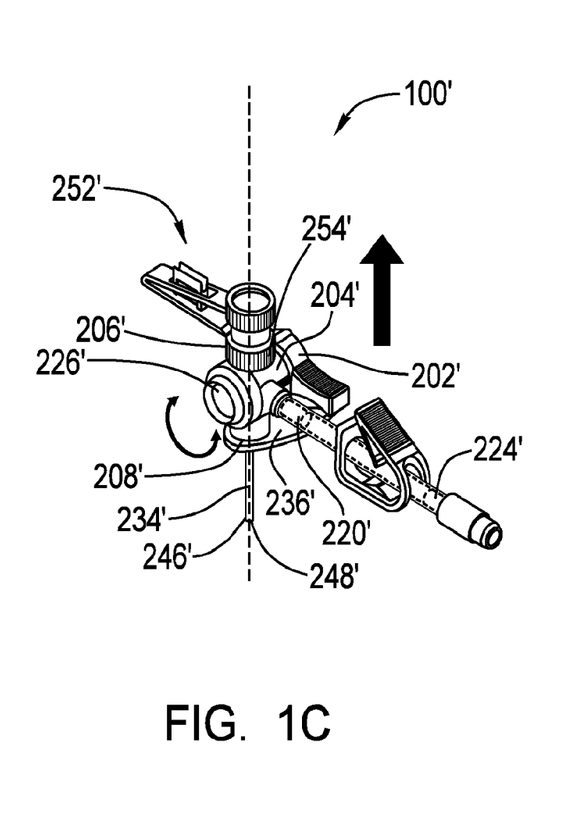
Figure 1D:
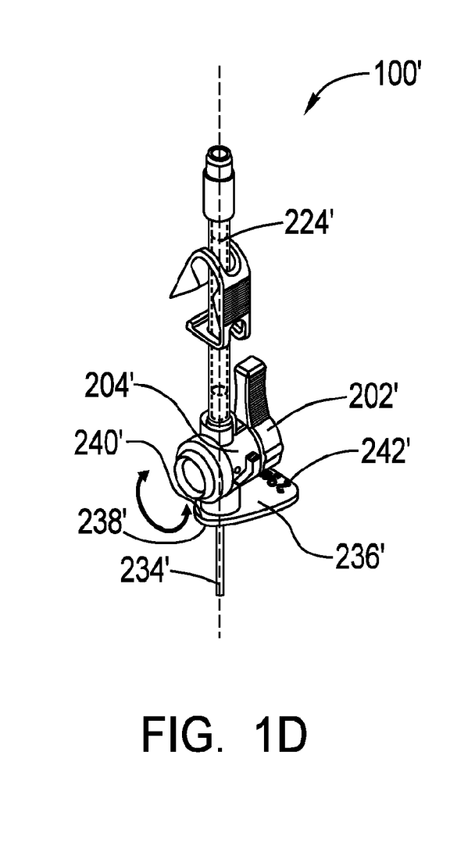

Referring now to FIGS. 1A-1D, with FIGS. 1C and 1D having elements numbers with primes for elements having similar counterparts in FIGS. 1A and 1B, aspects of the disclosed subject matter include a needle assembly 100 that includes a main housing 102, a connector housing 104, a plug 106 and a needle sub-assembly 108 all of which are configured to cooperate with one another.

Main housing 102 includes an obturator insertion opening 110 and an opposite needle connection opening 112.

Connector housing 104 includes an obturator opening 114, a tubing opening 116 and a plug opening 118. Connector housing 104 is configured to engage main housing 102.

Mug 106 is substantially self-sealing and includes a channel 120 formed through therethrough. Mug 106 is positioned within connector housing 104 so that channel 120 is aligned with tubing opening 116 or the connector housing.

Needle sub-assembly 108 includes a needle holder base 122 and a needle 124. Needle holder base 122 includes first and second surfaces 126 and 128 respectively. First surface 126 is configured to removably join with needle connection opening 112 in main housing 102 and needle 124 extends from second surface 128.

Connector housing 104 is configured to engage main housing 102 in a first position as shown in FIGS. 1A and 1B and in a second position as shown in FIGS. 1C and 1D, respectively. In the first position, obturator opening 114 of connector housing 104 is substantially axially aligned with obturator insertion opening 110 of main housing 102 and with needle 124. In the second position, tubing opening 116 of connector housing 104 is substantially axially aligned with obturator insertion opening 114 of main housing 104 and in fluid connection with needle 124.

Figure 2:
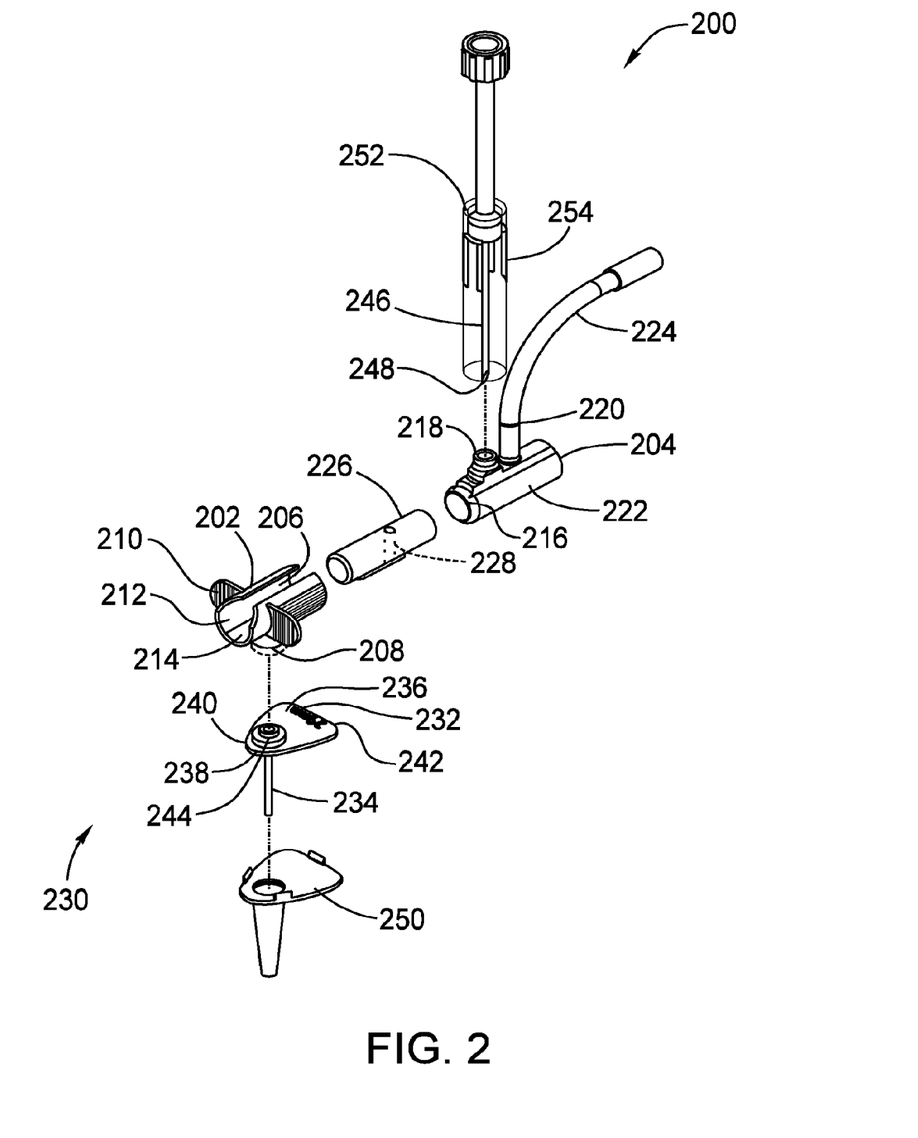
FIG. 2 is an exploded front isometric view of assemblies according to some embodiments of the disclosed subject matter.
Figures 3A, 3B, 3C, 3D:
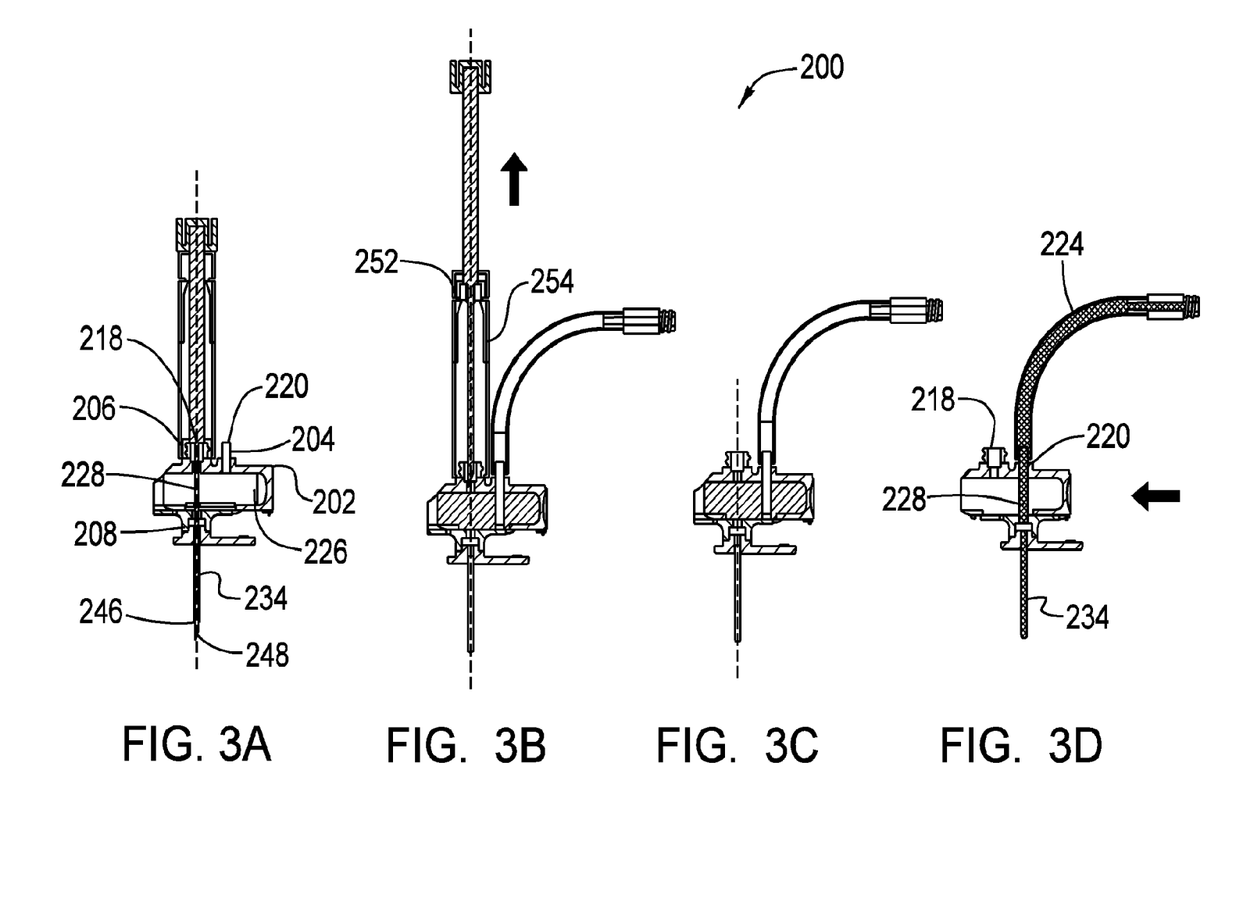
FIGS. 3A-3D are side section views of assemblies according to some embodiments of the disclosed subject matter.

Referring now to FIGS. 2 and 3, some embodiments include a needle assembly 200 include a main housing 202 and a slide connector housing 204 that are configured to slidably engage with one another. Main housing 202 includes a first opening 206 and a second opening 208. In some embodiments, main housing 202 includes protruding tabs 210 to facilitate handling assembly 200 and interior surfaces 212 having grooves 214 for engaging slide connector housing 204. In some embodiments, first opening 206 is a longitudinally extending opening.

Slide connector housing 204 is configured to slidably engage main housing 202, e.g., includes exterior surfaces 216 that are configured to slide within grooves 214 of main housing 202. Slide connector housing 204 includes an obturator opening 218, a tubing opening 220, and a plug opening 222. In some embodiments, assembly 200 includes tubing 224 for connection to tubing opening 220. Assembly 200 includes a substantially self-sealing plug 226 having a channel 228 formed therethrough. Plug 226 is positioned within slide connector housing 204 so channel 228 is aligned with tubing opening 220. In some embodiments, self-sealing plug 226 is formed substantially from silicone or a similar material.

Assembly 200 includes a needle sub-assembly 230 having a needle holder base 232 and a needle 234. Needle holder base 232 includes a first surface 236 that is configured to removably join with second opening 208 of main housing 202 and an opposite second surface 238 that needle 234 extends from. Needle holder base 232 is typically, but not always, asymmetrically shaped and in some embodiments includes a first side 240 and an opposite second side 242. Second side 242 is wider than first side 240 and needle 234 extends from second surface 238 at a position closer to the first side. In some embodiments, first surface 236 of needle holder base 232 includes a depth block portion 244 having a height that is predetermined according to a desired penetration depth of needle 234. Depth block portion 244 is configured, e.g., shaped or sized, to be removably joined with needle connection opening 208. Assembly 200 typically includes a needle 234 that is blunt and hollow and sized to concentrically receive an obturator 246 having a sharp end 248. Needle 234 is typically ultra-thin walled, e.g., about 15 gauge, and is typically siliconized inside and out. In some embodiments, assembly 200 includes removable needle and obturator covers 250 and 252, respectively, for covering needle 234 and obturator 246 before and after their use. As best shown in FIGS. 2 and 3B, in some embodiments, obturator cover 252 includes a detachable column 254 into which obturator 246 is passively withdrawn so that sharp end 248 of the obturator is completely covered after it is withdrawn thereby allowing it to be more safely handled while it is detached from assembly 200 and discarded.

Referring now to FIG. 3 and in particular to FIGS. 3A-3C, in a first position, slide connector housing 204 is slidably engaged with main housing 202 so that obturator 246 is substantially axially aligned with first opening 206 of the main housing and inserted through obturator opening 218, through first and second openings 206, 208 of the main housing, and into needle 234.

Referring now to FIG. 3D, in a second position, slide connector housing 204 is slidably engaged with main housing 202 with obturator 246 removed and the slide connector housing is positioned, e.g., by sliding the slide connector housing to the left, so that tubing opening 220 is substantially axially aligned with first and second openings 206, 208 of the main housing and in fluid connection with needle 234 via channel 228 in plug 226.

As shown in FIGS. 3A-3D and in particular in FIG. 3A, in use, assembly 200 including obturator 246 inserted in needle 234 with sharp end 248 extending from the needle is positioned by puncturing a patient's skin with the obturator and extending both the needle and obturator into an implanted port in the patient. Next, as shown in FIGS. 3B and 3C, obturator 246 is removed by pulling it up into obturator guard 252, both of which are subsequently removed from slide connector housing 204. Then, as shown in FIG. 3D, slide connector housing 204 is slid or moved to the left within main housing 202 so that tubing opening 220 is substantially axially aligned with first and second openings 206, 208 of the main housing and in fluid connection with needle 234 via channel 228 in plug 226. Blood can then flow to and from the patient through needle 234 and tubing 224.

Figure 4:
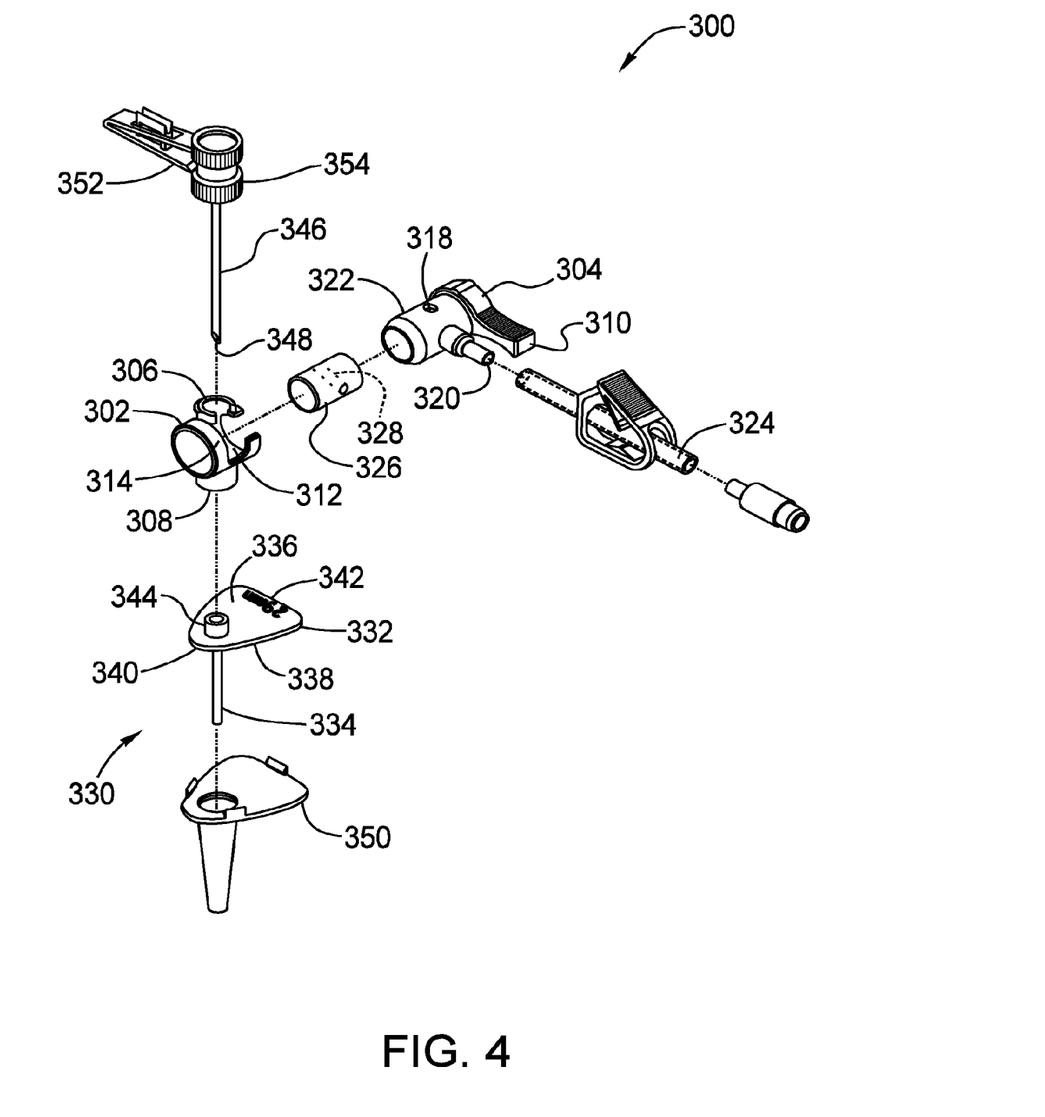
FIG. 4 is an exploded front isometric view of assemblies according to some embodiments of the disclosed subject matter.
Figure 5A:
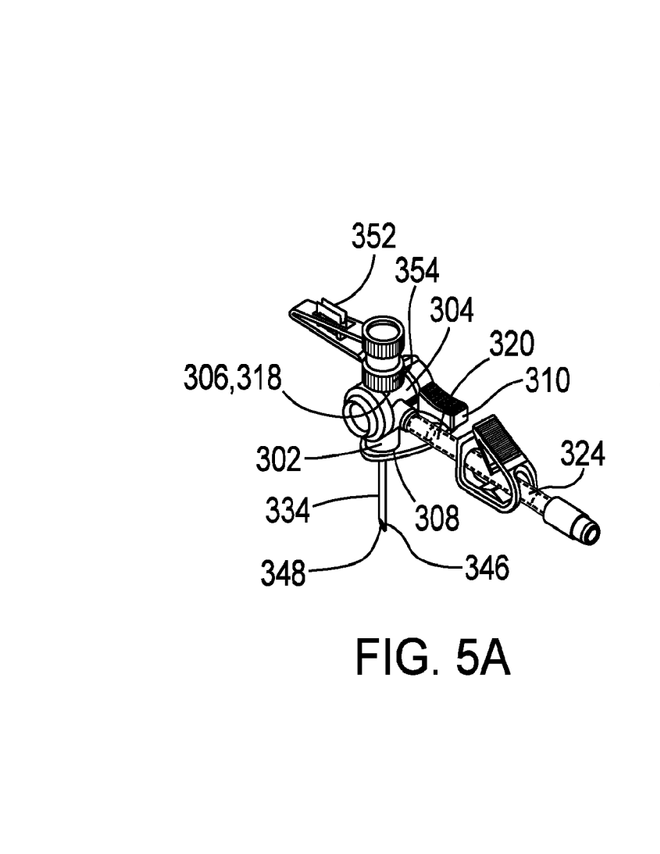
FIGS. 5A-5C are side section views of assemblies according to some embodiments of the disclosed subject matter.
Figure 5B:
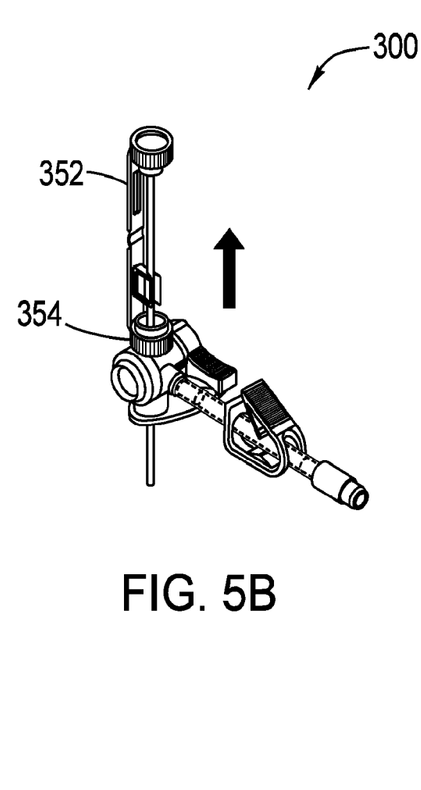
Figure 5C:
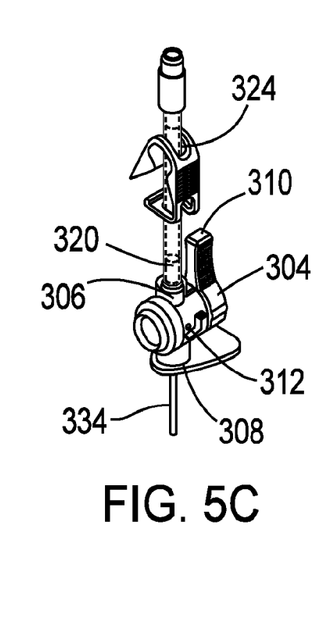

Referring now to FIGS. 4 and 5, some embodiments include a needle assembly 300 having a main housing 302 and a rotating connector housing 304 that are configured to rotatably engage with one another. Main housing 302 includes a first opening 306 and a second opening 308. In some embodiments, main housing 302 includes a handle 310 to facilitate handling assembly 300. In some embodiments, first opening 306 extends laterally and includes a slot 312 on a side 314 of main housing 302.

Rotating connector housing 304 is configured to rotatably engage main housing 302. For example, the main housing can be rotated within the connector housing by moving handle 310 up or down within first opening 306 and slot 312. Rotating connector housing 304 includes an obturator opening 318, a tubing opening 320, and a plug opening 322 that is aligned with the tubing opening. In some embodiments, assembly 300 includes tubing 324 for connection to tubing opening 220.

Assembly 300 includes a substantially self-sealing plug 326 having a channel 328 formed therethrough. Plug 326 is positioned within slide connector housing 304 so channel 328 is aligned with tubing opening 320. In some embodiments, self-sealing plug 326 is formed substantially from silicone or a similar material.

Assembly 300 includes a needle sub-assembly 330 having a needle holder base 332 and a needle 334. Needle holder base 332 includes a first surface 336 that is configured to removably join with second opening 308 of main housing 302 and an opposite second surface 338 that needle 334 extends from. Needle holder base 332 is typically, but not always, asymmetrically shaped and in some embodiments includes a first side 340 and an opposite second side 342. Second side 342 is wider than first side 340 and needle 334 extends from second surface 338 at a position closer to the first side. In some embodiments, first surface 336 of needle holder base 332 includes a depth block portion 344 having a height that is predetermined according to a desired penetration depth of needle 334. Depth block portion 344 is configured, e.g., shaped or sized, to be removably joined with needle connection opening 308. Assembly 300 typically includes a needle 334 that is blunt and hollow and sized to receive an obturator 346 having a sharp end 348. In some embodiments, assembly 300 includes removable needle and obturator covers 350 and 352, respectively, for covering needle 334 and obturator 346 before and after their use. As best shown in FIGS. 4 and 5B, in some embodiments, obturator cover 352 includes a sliding obturator end cover 354 into which sharp end 348 of obturator 346 is withdrawn so that the sharp end is completely covered after it is withdrawn thereby allowing it to be more safely handled while it is detached from assembly 300 and discarded.

Referring now to FIG. 5 and in particular to FIGS. 5A and 5B, in a first position, rotating connector housing 304 is rotatably engaged with main housing 302 so that obturator 346 is substantially axially aligned with first opening 306 of the main housing and inserted through obturator opening 318, through first and second openings 306, 308 of the main housing, and into needle 334.

Referring now to FIG. 5C, in a second position, rotating connector housing 304 is rotatably engaged with main housing 302 with obturator 346 removed and the rotating connector housing is positioned, e.g., by grasping handle 310 and pushing the handle upwardly (as indicated by arrow in FIG. 5B) thereby rotating the rotating connector housing so that tubing opening 320 is substantially axially aligned with first and second openings 306, 308 of the main housing and in fluid connection with needle 334 via channel 328 in plug 326 (as shown best in FIG. 4).

As shown in FIGS. 5A-5C and in particular in FIG. 5A, in use, assembly 300 including obturator 346 inserted in needle 334 with sharp end 348 extending from the needle is positioned by puncturing a patient's skin with the obturator and extending both the needle and obturator into an implanted port in the patient. Next, as shown in FIG. 5B, obturator 346 is removed by pulling it up and into obturator guard 352, both of which are subsequently removed from rotating connector housing 304. Then, as shown in FIG. 5C, rotating connector housing 304 is rotated by grasping handle 310 and pushing the handle upwardly (as indicated by arrow in FIG. 5B) thereby rotating the rotating connector housing within main housing 302 so that tubing opening 320 is substantially axially aligned with first and second openings 306, 308 of the main housing and in fluid connection with needle 334 via channel 328 in plug 326 (as shown best in FIG. 4). Blood can then flow to and from the patient through needle 334 and tubing 324.

Needle assemblies according to the disclosed subject matter offer benefits over known designs. In addition to including safety features such as unique obturator and needle covers, which are not included in prior art designs, assemblies according to the disclosed subject matter include mechanisms for placing blood tubing in fluid communication with the needle after inserting the needle and removing the obturator. Such mechanisms allow blood flowing to and from the needle and tubing to avoid having to navigate through a serpentine pathway.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A needle assembly comprising:
a main housing including an obturator insertion opening and an opposite needle connection opening;
a connector housing configured to engage said main housing, said connector housing including an obturator opening, a tubing opening, and a plug opening;
a substantially self-sealing plug including a channel formed therethrough, said plug positioned within said connector housing so said channel is aligned with said tubing opening; and a needle sub-assembly having a needle holder base and a needle, said needle holder base including first and second surfaces, said first surface configured to removably join with said needle connection opening and said second surface having said needle extending therefrom;

wherein said connector housing is configured to engage said main housing in first and second positions, said obturator opening being substantially axially aligned with said obturator insertion opening and substantially axially aligned with said needle in said first position, and said tubing opening being substantially axially aligned with said obturator insertion opening and in fluid connection with said needle in said second position.

2. The assembly according to claim 1, wherein said connector housing is configured to slidably engage said main housing.

3. The assembly according to claim 1, wherein said connector housing is configured to rotatably engage said main housing.

4. The assembly according to claim 1, further comprising an obturator sized to fit within said obturator opening and said needle.

5. The assembly according to claim 4, wherein said obturator includes a substantially sharp end.

6. The assembly according to claim 4, wherein said needle is a blunt hollow needle and sized to receive said obturator.

7. The assembly according to claim 1, wherein said main housing includes protruding tabs and a longitudinally extending opening.

8. The assembly according to claim 1, wherein said self-sealing plug is formed substantially from silicone.

9. The assembly according to claim 1, wherein said first surface of said needle holder base includes a depth block portion having a height that is predetermined according to a desired penetration depth of said needle, said depth block portion configured to be removably joined with said needle connection opening.

10. The assembly according to claim 1, wherein said needle holder base is asymmetrically shaped and includes a first side and an opposite second side, said second side being wider than said first side and said needle extending from said second surface at a position closer to said first side.

11. The assembly according to claim 1, further comprising a removable needle cover.

12. The assembly according to claim 1, further comprising a removable obturator cover.

13. The assembly according to claim 1, further comprising tubing for connection to said tubing opening.

14. A needle assembly comprising:
a main housing including at least first and second openings;
a slide connector housing configured to slidably engage said main housing, said slide connector housing including an obturator opening, a tubing opening, and a plug opening;
a substantially self-sealing plug including a channel formed therethrough, said plug positioned within said slide connector housing so said channel is aligned with said tubing opening;
a needle sub-assembly including a needle holder base and a needle, said needle holder base having a first surface that is configured to removably join with said second opening of said main housing and an opposite second surface with said needle extending therefrom; and
an obturator sized to fit within said obturator opening and said needle;
wherein in a first position, said slide connector housing includes exterior surfaces and said main housing includes interior surfaces that are configured to allow said slide connector housing to slidably engage said main housing so that said obturator is substantially axially aligned with said first opening of said main housing and inserted through said obturator opening, through said first and second openings of said main housing, and into said needle, and wherein in a second position, said slide connector housing exterior surfaces and said main housing interior surfaces are configured to allow said slide connector housing to slidably engage said main housing with said obturator removed and said slide connector housing positioned so that said tubing opening is substantially axially aligned with said first and second openings in said main housing and in fluid connection with said needle.

15. The assembly according to claim 14, wherein said first surface of said needle holder base includes a depth block portion having a height that is predetermined according to a desired penetration depth of said needle, said depth block portion configured to be removably joined with said needle connection opening.

16. The assembly according to claim 14, wherein said needle holder base is asymmetrically shaped and includes a first side and an opposite second side, said second side being wider than said first side and said needle extending from said second surface at a position closer to said first side.

17. A needle assembly comprising:
a main housing including at least first and second openings;
a rotating connector housing configured to rotatably engage said main housing, said rotating connector housing including an obturator opening, a tubing opening, and a plug opening;
a substantially self-sealing plug including a channel formed therethrough, said plug positioned within said rotating connector housing so said channel is aligned with said tubing opening;
a needle sub-assembly including a needle holder base and a needle, said needle
holder base having a first surface that is configured to removably join with said second opening of said main housing and an opposite second surface with said needle extending therefrom; and
an obturator sized to fit within said obturator opening and said needle;
wherein said rotating connector housing includes exterior surfaces, said main housing includes interior surfaces, and said exterior and interior surfaces are configured to engage rotatably engage said rotating connector housing and said main housing in first and second positions, in said first position, said obturator is substantially axially aligned with said first opening of said main housing and inserted through said first opening of said main housing, through said obturator opening, through said second opening of said main housing, and into said needle, and in said second position, said obturator is removed and said tubing opening is substantially axially aligned with said first and second openings in said main housing and in fluid connection with said needle.

18. The assembly according to claim 17, wherein said first surface of said needle holder base includes a depth block portion having a height that is predetermined according to a desired penetration depth of said needle, said depth block portion configured to be removably joined with said needle connection opening.

19. The assembly according to claim 17, wherein said needle holder base is asymmetrically shaped and includes a first side and an opposite second side, said second side being wider than said first side and said needle extending from said second surface at a position closer to said first side.

20. The assembly according to claim 17, further comprising a removable obturator cover.

* * * * *